(12) United States Patent
Matson et al.

(10) Patent No.: US 9,522,864 B2
(45) Date of Patent: *Dec. 20, 2016

(54) PROCESS FOR DIRECT CONVERSION OF BIOMASS TO LIQUID FUELS AND CHEMICALS

(71) Applicant: The Regents of the University of California, Oakland, CA (US)

(72) Inventors: Theodore D. Matson, Goleta, CA (US); Peter C. Ford, Santa Barbara, CA (US); Gerald Macala, Santa Barbara, CA (US); Alexei Iretski, Sault Sainte Marie, MI (US)

(73) Assignee: The Regents of the University of California, Oakland, CA (US)

( * ) Notice: Subject to any disclaimer, the term of this patent is extended or adjusted under 35 U.S.C. 154(b) by 260 days.

This patent is subject to a terminal disclaimer.

(21) Appl. No.: 14/323,264

(22) Filed: Jul. 3, 2014

(65) Prior Publication Data

US 2014/0343174 A1    Nov. 20, 2014

Related U.S. Application Data

(63) Continuation of application No. 12/885,397, filed on Sep. 17, 2010, now Pat. No. 8,796,494.
(Continued)

(51) Int. Cl.
*C07C 1/00* (2006.01)
*C07C 29/151* (2006.01)
(Continued)

(52) U.S. Cl.
CPC ............. *C07C 29/1518* (2013.01); *C01B 3/22* (2013.01); *C10J 3/00* (2013.01); *C10L 1/02* (2013.01);
(Continued)

(58) Field of Classification Search
CPC ................................. C07C 1/00; Y02E 50/17
(Continued)

(56) References Cited

U.S. PATENT DOCUMENTS 5,959,167 A * 9/1999 Shabtai .................. C10G 1/002
585/240
6,172,272 B1 * 1/2001 Shabtai .................. C10G 1/002
208/108
(Continued)

*Primary Examiner* — Nina Bhat
(74) *Attorney, Agent, or Firm* — Berliner & Associates

(57) ABSTRACT

A method of catalytically preparing a fluid product from solid carbonaceous material is described. In the method, at least one of the following equilibria is established by one or more catalysts: a) $CH_3OH \rightleftharpoons CO+2H_2$, b) $CO+H_2O \rightleftharpoons CO_2+H_2$. In some versions, the solid carbonaceous material is woody biomass. Components of the fluid product can include one or a combination of $C_5$-$C_9$ alcohols. In certain versions, the method can be practiced with substantially all of the carbon in the carbonaceous material being converted to the fluid product. Also, in some versions, the fluid product can be prepared with substantially no char formation. The fluid product of various versions can be used directly as fuel or as a reagent for preparing commodity chemicals without the need for separating the fluid product components.

24 Claims, 3 Drawing Sheets

Related U.S. Application Data

(60) Provisional application No. 61/243,343, filed on Sep. 17, 2009.

(51) Int. Cl.
*C01B 3/22* (2006.01)
*C10J 3/00* (2006.01)
*C10L 1/02* (2006.01)
*B01J 23/80* (2006.01)

(52) U.S. Cl.
CPC ......... *B01J 23/80* (2013.01); *C01B 2203/0277* (2013.01); *C01B 2203/0283* (2013.01); *C01B 2203/1041* (2013.01); *C01B 2203/1076* (2013.01); *C01B 2203/1082* (2013.01); *C01B 2203/1094* (2013.01); *C01B 2203/1223* (2013.01); *C10G 2300/1011* (2013.01); *C10J 2300/0916* (2013.01); *C10J 2300/0986* (2013.01); *C10J 2300/0989* (2013.01); *Y02E 50/18* (2013.01); *Y02E 50/32* (2013.01); *Y02P 30/20* (2015.11)

(58) Field of Classification Search
USPC .......................................... 585/240; 44/606
See application file for complete search history.

(56) References Cited

U.S. PATENT DOCUMENTS

| | | | | |
|---|---|---|---|---|
| 7,964,761 | B2* | 6/2011 | Zmierczak | C10G 1/002 44/605 |
| 8,796,494 | B2* | 8/2014 | Matson | C01B 3/22 44/307 |
| 8,871,989 | B2* | 10/2014 | Chen | C10G 1/002 585/240 |
| 2010/0312027 | A1* | 12/2010 | Tsurutani | C10G 1/002 585/242 |

* cited by examiner

PROCESS FOR DIRECT CONVERSION OF BIOMASS TO LIQUID FUELS AND CHEMICALS

CROSS-REFERENCE TO RELATED APPLICATIONS

This application claims the benefit of U.S. patent application Ser. No. 12/885,397, filed Sep. 17, 2010, which claims the benefit of Provisional Patent Application No. 61/243,343, filed on Sep. 17, 2009, which is incorporated by reference herein.

STATEMENT REGARDING FEDERALLY SPONSORED RESEARCH OR DEVELOPEMENT

This invention was made with Government support under NSF Cooperative Agreement CHE-0650456 and Grant No. O1SE-0530268 from the National Science Foundation. The Government has certain rights in this invention.

BACKGROUND

Field of the Invention

The invention relates to methods for converting carbonaceous materials into liquid and gaseous products.

Related Art

Biomass is the only renewable source of carbon on earth and what is termed "lignocellulosic biomass" or "woody biomass"—material composed almost exclusively of the distinct polymers cellulose, hemicellulose, lignin, and lignocellulose—is the most abundant form of biomass. It is estimated that $1.3 \times 10^{12}$ kg/yr of these materials could be sustainably produced in the United States without compromising the supply of building materials or food. As of April, 2005 production of these materials was roughly $1.8 \times 10^{11}$ kg/yr in the United States (1).

Historically there are three approaches to the production of liquid fuels and commodity chemicals from woody biomass: gasification, pyrolysis, or hydrolysis (2). Pyrolysis and gasification involve heating raw biomass to select for either liquids or gases, respectively. They are non-selective processes. They are attractive because they produce a ready-to-go product (in poor yield) such as "bio-oil" or syn gas, the latter of which is attractive because of the large chemical infrastructure already in place for its utilization. However, both processes produce a large quantity of char, which has been described as "the most cumbersome and problematic parameter in any gasification commercialization effort" (3).

Hydrolysis refers to the specific efforts to use near- and supercritical water to convert cellulose and hemicellulose to fermentable sugars and assumes that the lignin thus produced will be treated separately. The problems with hydrolysis are two-fold: water must be separated from the final product, and the chemical bonds that compose woody biomass, especially aryl ethers, are inherently resistant to hydrolysis.

Representative of the state of the art is the flow chart depicted in FIG. 1 (taken from the Huber review, Ref. 2).

SUMMARY

A catalytic method for converting solid carbonaceous material, including processed or unprocessed biomass (containing lignin, cellulose, hemicellulose or lignocellulose, or any combination thereof), into liquid and gaseous products is provided. The method includes at least one catalyst that establishes one or both of the following equilibria: a) $CH_3OH = CO + 2H_2$; b) $CO + H_2O = CO_2 + H_2$.

In certain embodiments, methanol at temperatures in excess of its critical temperature $T_c = 240°$ C.) is used as a solvent and source of the reducing gases hydrogen and carbon monoxide. Some of the products can include higher aliphatic alcohols ($C_5$-$C_9$), hydrogen, carbon monoxide, methane, and carbon dioxide. In some embodiments, a Cu-doped metal oxide catalyst establishes one or both of the methanol synthesis $CH_3OH = CO + 2H_2$ and water gas shift $CO + H_2O = CO_2 + H_2$ equilibria. This catalyst, or other catalysts in other embodiments, can further act to depolymerize lignin and/or lignocellulose in the biomass by aryl ether hydrogenolysis, and act on the reaction products to hydrogenate oxygenated aromatic rings, and to dehydrate and hydrogenate reaction products to produce chemical compounds such as methane and alkylcyclohexanols with concomitant loss of water. This catalyst, or other catalysts in other embodiments, can also act to depolymerize cellulose, hemicellulose, and/or lignocellulose, and act to extensively dehydrate and hydrogenate the reaction products to produce chemical compounds such as isomers of pentanol and hexanol with concomitant loss of water. Dehydration of lignin-, cellulose-, hemicellulose-, and lignocellulose-derived chemicals and materials produces unsaturated intermediates, and the unsaturated intermediates are rapidly hydrogenated, preventing over-dehydration of the materials and chemicals to char.

The catalytic method described herein can obviate the need for separation since fuel production is accomplished by the reaction of biomass+methanol->higher aliphatic alcohols+synthesis gas. As used herein, synthesis gas refers to a mixture of hydrogen, carbon monoxide, carbon dioxide, and methane. Furthermore, the energy wasted in biomass transport can be reduced dramatically if reducing equivalents are regenerated from cellulose in this reaction.

In accordance with various embodiments of this invention, the catalytic method can wholly convert insoluble solid biomass to soluble materials and gases, thus eliminating the need for separations. Further, the soluble materials produced by the method can be converted to commodity chemicals or a mixture of chemicals suitable for combustion in unmodified internal combustion engines Thus, some embodiments can address the goal of reducing demand for petroleum-derived chemicals and fuels, and reducing emissions of carbon dioxide.

BRIEF DESCRIPTION OF THE DRAWINGS

For a more complete understanding of the present invention, reference is now made to the following descriptions taken in conjunction with the accompanying drawings, in which.

DETAILED DESCRIPTION

Figure 1:
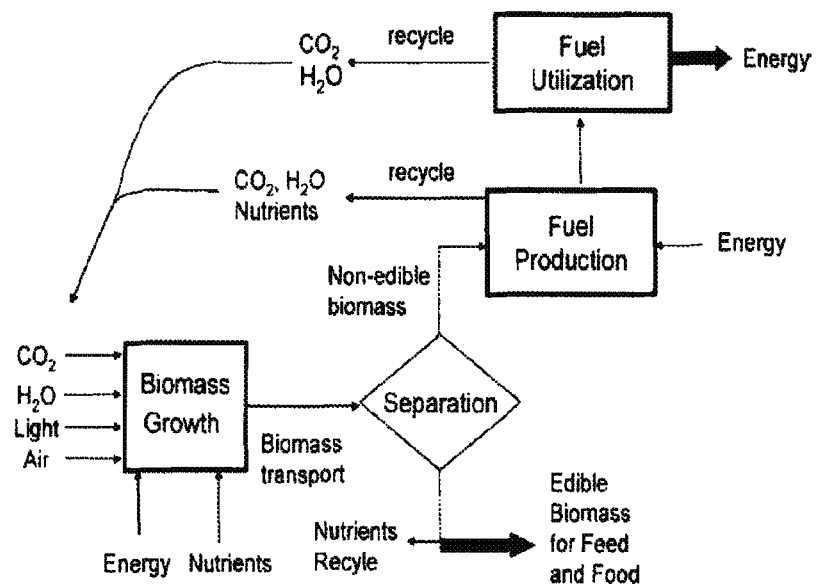
FIG. 1 is a flow-chart showing the current state of liquid fuel production from biomass.

In one aspect, a method of catalytically preparing a fluid product from solid carbonaceous material is provided. The method comprises reacting solid carbonaceous material in the presence of one or more first catalysts to produce soluble material under conditions in which at least one of the following equilibria is established by one or more first catalysts:

$$CH_3OH \rightleftharpoons CO + 2H_2; \quad \text{a)}$$

$$CO + H_2O \rightleftharpoons CO_2 H_2; \quad \text{b)}$$

The method can further comprise depolymerizing polymeric material in the presence of one or more depolymerization catalysts, where the polymeric material is contained in or derived from the solid carbonaceous material. Together with or separately from the depolymerizing reactions, the method can also comprise dehydrating chemical compounds in the presence of one or more dehydration catalysts, where the chemical compounds are derived from the solid carbonaceous material. Together with or separately from the depolymerizing and/or dehydration reactions, the method can also comprise hydrogenating chemical intermediates in the presence of one or more hydrogenation catalysts, where the chemical intermediates are derived from the solid carbonaceous material. One result of applying the method is preparation of a fluid product.

In some embodiments, the solid carbonaceous material is biomass, which can be woody biomass.

The one or more first catalysts of various embodiments of the method, including any embodiments described in the paragraphs above, can comprise a Cu-doped metal oxide, a zeolite catalyst, a supported metal catalyst, a metal carbide catalyst, or any combination thereof. The one or more depolymerization catalysts can comprise a copper-doped metal oxide catalyst or a supported metal catalyst, or any combination thereof. The one or more dehydration catalysts can comprise a Cu-doped metal oxide or a zeolite catalyst, or any combination thereof. Also, the one or more hydrogenation catalysts can comprise a Cu-doped metal oxide, a supported metal catalyst or a metal carbide catalyst, or any combination thereof. In addition, the one or more first catalysts, the one or more depolymerization catalysts, the one or more dehydration catalysts, and the one or more hydrogenation catalysts can be the same catalyst, such as one comprising mixed oxides of Cu/Mg/Al or Cu/ZnO/Al$_2$O$_3$. In any embodiment including a Cu-doped metal oxide, the catalyst can comprise oxides of Cu, M(II), and/or M(III) in any proportion, wherein M(II) is selected from either Mg and/or Zn, and M(III) is selected from either Al, Cr, and/or Fe. In any embodiment including a supported metal catalyst, the catalyst can be Pt/Al$_2$O$_3$, Rh/ZrO$_2$, Pd/C, or Cu/hydrotalcite. In any embodiment including a metal carbide catalyst, the catalyst may be W$_2$C supported on activated carbon. In any embodiment including a zeolite catalyst, the catalyst may be H-ZSM-5.

In any embodiment that includes carbonaceous material containing lignin, cellulose, hemicellulose or lignocellulose, or any combination thereof, products of the method (including soluble products) can be derived from the lignin, cellulose, hemicellulose or lignocellulose, or any combination thereof. Examples of soluble products include, but are not limited to:

(a) polysaccharides and/or polyaromatics and/or copolymers thereof;

(b) unsaturated methylated glycosides, sugars and/or molecules, all with empirical formulas defined by $C_nH_{2n-x}(OR)_x$ with R=H, CH$_3$, n≥4, and x≤n;

(c) saturated methylglycosides, sugar alcohols and/or molecules with empirical formulas represented by $C_nH_{2n+2-x}(OR)_x$ where R=H, CH$_3$, n=4,5,6, and x≤n;

(d) saturated higher alcohols with formulas defined by $C_nH_{2n+2}O$ with n=5, 6;

(e) alkylcyclohexanols with empirical formulas represented by $C_nH_{2n-6}O_x$ where n=8, 9 and x=1, 2, 3;

(f) aromatic compounds with empirical formulas represented by $C_nH_{2n-6}O_x$ where n=8, 9 and x=0, 1, 2, 3;

(g) saturated alkanes with empirical formulas represented by $C_nH_{2n+2}$ where n≥1; and/or (h) alkylcyclohexanes with empirical formulas represented by $C_nH_{2n}$ where n=8, 9.

In another aspect, a method of catalytically preparing a fluid product from biomass is provided. The method comprises reacting a biomass material in a reducing environment in the presence of methanol and one or more catalysts so as to produce a fluid product, wherein the one or more catalysts establish at least one of the following equilibria: a) $CH_3OH \rightleftharpoons CO + 2H_2$; b) $CO + H_2O \rightleftharpoons CO_2 + H_2$. In some embodiments, the biomass can be woody biomass.

In any embodiments that include biomass, the one or more catalysts can comprise a Cu-doped metal oxide, a zeolite catalyst, a supported metal catalyst, a metal carbide catalyst, or any combination thereof. In any embodiment including a Cu-doped metal oxide, the catalyst can comprise oxides of Cu, M(II), and/or M(III) in any proportion, wherein M(II) is selected from Mg and/or Zn, and M(III) is selected from Al, Cr, and/or Fe. In any embodiment including a zeolite catalyst, the catalyst may be H-ZSM-5. In any embodiment including a supported metal catalyst, the catalyst can be Pt/Al$_2$O$_3$, Rh/ZrO$_2$, Pd/C, or Cu/hydrotalcite. In any embodiment including a metal carbide catalyst, the catalyst may be W$_2$C supported on activated carbon.

Embodiments that include biomass can further comprise: depolymerizing polymeric material in the presence of one or more depolymerization catalysts, the polymeric material contained in or derived from the biomass; or dehydrating chemical compounds in the presence of one or more dehydration catalysts, the chemical compounds derived from the biomass; or hydrogenating chemical intermediates in the presence of one or more hydrogenation catalysts, the chemical intermediates derived from the biomass; or a combination thereof.

The one or more depolymerization catalysts can comprise a copper-doped metal oxide catalyst or a supported metal catalyst, or any combination thereof. The one or more dehydration catalysts can comprise a Cu-doped metal oxide or a zeolite catalyst, or any combination thereof. Also, the one or more hydrogenation catalysts can comprise a Cu-doped metal oxide, a supported metal catalyst or a metal carbide catalyst, or any combination thereof. In any embodiment including a Cu-doped metal oxide, the catalyst can comprise oxides of Cu, M(II), and/or M(III) in any proportion, wherein M(II) is selected from either Mg and/or Zn, and M(III) is selected from either Al, Cr, and/or Fe. In any embodiment including a supported metal catalyst, the catalyst can be Pt/Al$_2$O$_3$, Rh/ZrO$_2$, Pd/C, or Cu/hydrotalcite. In any embodiment including a metal carbide catalyst, the catalyst may be W$_2$C, supported on activated carbon. In any embodiment including a zeolite catalyst, the catalyst may be H-ZSM-5.

In some embodiments, the one or more catalysts, the one or more depolymerization catalysts, the one or more dehydration catalysts, and the one or more hydrogenation catalysts are the same catalyst, which in some embodiments comprise mixed oxides of Cu/Mg/Al or Cu/ZnO/Al$_2$O$_3$.

In some embodiments, a cosolvent can replace methanol or be added in addition to methanol, depending on the reaction conditions and the amount of reaction components. Examples of cosolvents include, but are not limited to, generally inert chemicals such as pentane or other saturated chain alkanes, and fluid products derived from other embodiments such as saturated higher alcohols and alkylcyclohexanols. Also, in certain embodiments, CO and $H_2$ can replace methanol or be added in addition to methanol, depending on the reaction conditions and the amount of reaction components.

Examples of solid carbonaceous material include, but are not limited to, coal and other mineral fuels, plastics, methanol-soluble Kraft lignin extract, alkali lignin (Aldrich 471003), byproduct lignin from paper production, lignite, and biomass. Biomass can include plant or animal matter such as manure, municipal waste, woody biomass, seed or vegetable oils, food waste, forestry waste, paper waste, cardboard waste, or construction debris. Examples of woody biomass include, but are not limited to, wood, sawdust, agricultural waste, forestry waste, cardboard, paper, corn stover, straws, and grasses. In any embodiment, the solid carbonaceous material can be mixed with non-carbonaceous material. Also, in any embodiment, combinations of different solid carbonaceous material can be used in practicing the invention.

In any embodiment of the invention, including any embodiments described in the paragraphs above, the following features and any combination of the features can apply:

a) the methods can be carried out at a temperature of about 100° C., to about 700° C.;
b) the methods can be carried out at a temperature at or above the critical temperature of methanol;
c) the fluid product can comprise a gas and/or a liquid;
d) the fluid product can comprise chemical compounds derived from cellulose, hemicellulose or lignocellulose, or any combination thereof, and/or chemical compounds derived from lignin;
e) the fluid product can comprise a $C_5$, $C_6$, $C_7$, $C_8$ or $C_9$ alcohol, or a combination thereof;
f) the fluid product can comprise a syn gas mixture; a syn gas mixture refers to a mixture comprising hydrogen, carbon monoxide, carbon dioxide, and methane;
g) the fluid product can comprise aromatic chemicals derived from lignin, cellulose, hemicellulose or lignocellulose, or any combination thereof;
h) a component of the fluid product can be used as fuel or as a reagent for chemical synthesis;
i) the fluid product can comprise a high-octane gasoline additive containing methanol and $C_5$-$C_9$ aliphatic alcohols;
j) substantially all of the carbon content of the solid carbonaceous material can be converted into components of the fluid product; the term "substantially all" means at least 97%, 97.5%, 98%, 98.5%, 99%, or 99.5% of the carbon atoms in the solid carbonaceous material are converted into components of the fluid product;
k) the fluid product can be prepared with substantially no char formation. The term "substantially no char formation" means less than 3.0%, 2.5%, 2%, 1.5%, 1% or 0.5% of the carbon atoms initially present in the solid carbonaceous material are recovered as insoluble char;
l) the fluid product can be used directly for fuel or chemical synthesis without separating components of the fluid product;
m) methanol that is degraded in the methods can be recovered by further processing.

Figure 2:
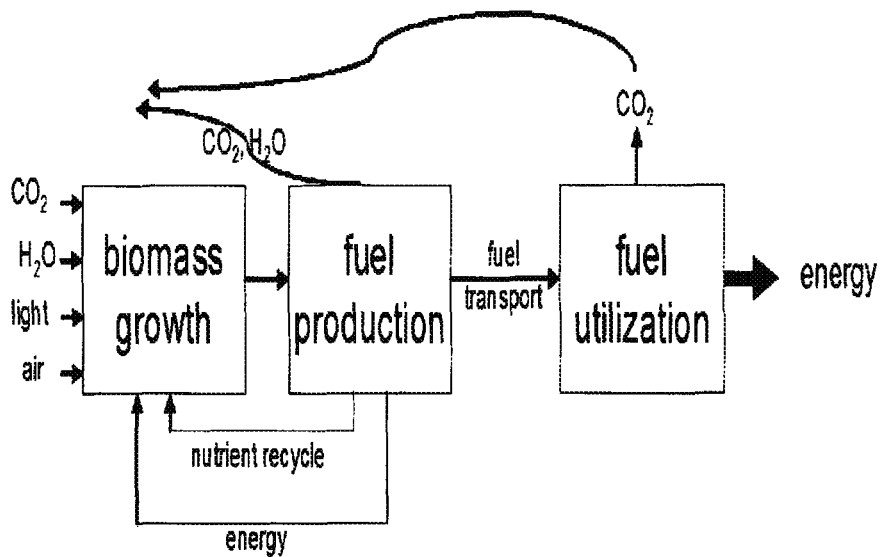
FIG. 2 is a flow-chart showing the biomass to fuel conversion based on a catalytic method.

Embodiments of the invention can be represented by the flow chart in FIG. 2.

The inventors are not aware of any process that produces internal combustion engine-ready fuel or fuel additive from biomass without the need for separation at any point in the process By suppressing char, various embodiments of the invention are able to use thermal means to convert essentially 100% of the carbon content of raw biomass to liquid and gaseous materials of potentially high value, a process that is without precedent. The entire approach differs markedly from previously reported methods in that chemical separation is not necessary at any stage.

This process can be applied to other materials containing the polymers lignin, cellulose, hemicellulose, and/or lignocellulose—e.g. eucalyptus, switchgrass, agricultural waste, waste cardboard, etc. Also, other catalysts can be added to alter product distribution, and the addition of these other catalysts still relies on the fundamental novelty of quantitative phase transfer.

In some embodiments, some or all of the methanol may be recovered by retro-aldol condensation of cellulose-derived unsaturated chemical compounds containing a terminal hydroxyl group in a position gamma to a carbonyl carbon followed by hydrogenation of the resulting carbonyl-containing compounds. Compounds containing a terminal hydroxyl group in a position gamma to a carbonyl carbon include, but are not limited to, unsaturated methyl glycosides and unsaturated compounds of the general formula $C_nH_{2n}O_{n-x}$ wherein n≥3 and 2≤x<n.

The one or more catalysts used in various embodiments may be used to effect retro-aldol condensation.

The present invention may be better understood by referring to the accompanying examples, which are intended for illustration purposes only and should not in any sense be construed as limiting the scope of the invention.

Example 1

Materials

Maple sawdust was obtained as a byproduct of sanding the corresponding oven-dried lumber using 80 grit sandpaper. A large representative sample (>100 g) was collected. The fraction of the powder (>95%) that passed across a 63μ screen (>230 mesh) was used without further modification. A ternary metal oxide catalyst Cu/Mg/Al with 15/60/25 molar ratio (Cu20-PMO), known to be active for enforcing the $CH_3OH \rightleftharpoons CO+2H_2$ and $CO+H_2O \rightleftharpoons CO_2+H_2$ equilibria and for aryl ether hydrogenolysis, was prepared according to a published procedure (4).

Experimental Procedures

A 10 mL Swagelok union was charged with 100 mg of Cu20-PMO, 100 mg of maple sawdust, 2.4 g $CH_3OH$, purged with argon, sealed, weighed and placed in a preheated aluminum block at 300° C. for 24 hours. The reactor was then rapidly cooled to room temperature and weighed. Data were discarded if the post-reaction weight deviated by more than 10 mg from the pre-reaction weight.

A small aliquot of the liquid product was separated from the solids by gravity filtration through a pre-weighed fritted funnel and analyzed by gas chromatography with a flame ionization detector (GC-FID). The remaining solids were then dislodged from the reactor onto the frit using copious methanol, subsequently washed with diethyl ether and pentane, and thoroughly dried. To assess the extent of conversion, the solids were transferred to a vial, slurried with water, slowly treated with concentrated nitric acid under vigorous stirring to selectively dissolve metallic copper and non-silicaceous inorganic oxides, returned to the fritted filter, dried, and reweighed.

A mixture containing 575 mg of $H_2/CO/CO_2/CH_4$ and other volatile organic compounds (VOC's) was expelled upon opening. The clear, colorless methanolic solution was analyzed by GC-FID and found to contain unreacted methanol, a mixture of $C_2$-$C_6$ alcohols and other products assumed to be ethers thereof, eluting between 3 and 10 minutes (HAE), and products eluting after 10 minutes identified as cyclohexyl alcohols and partially-etherified products containing between 9 and 12 carbons (CAE). Based on integration, this corresponded to a solution of roughly 4.6 and 1.8 wt % of HAE and CAE in methanol, respectively. The 96 mg of blackish red solid product dissolved upon acid titration as described above, leaving a very small quantity (<1 mg) of a colorless, flocculent solid. This implies quantitative conversion of the carbonaceous substrate and the absence of intractable organic solids (char).

Example 2

Figure 3:
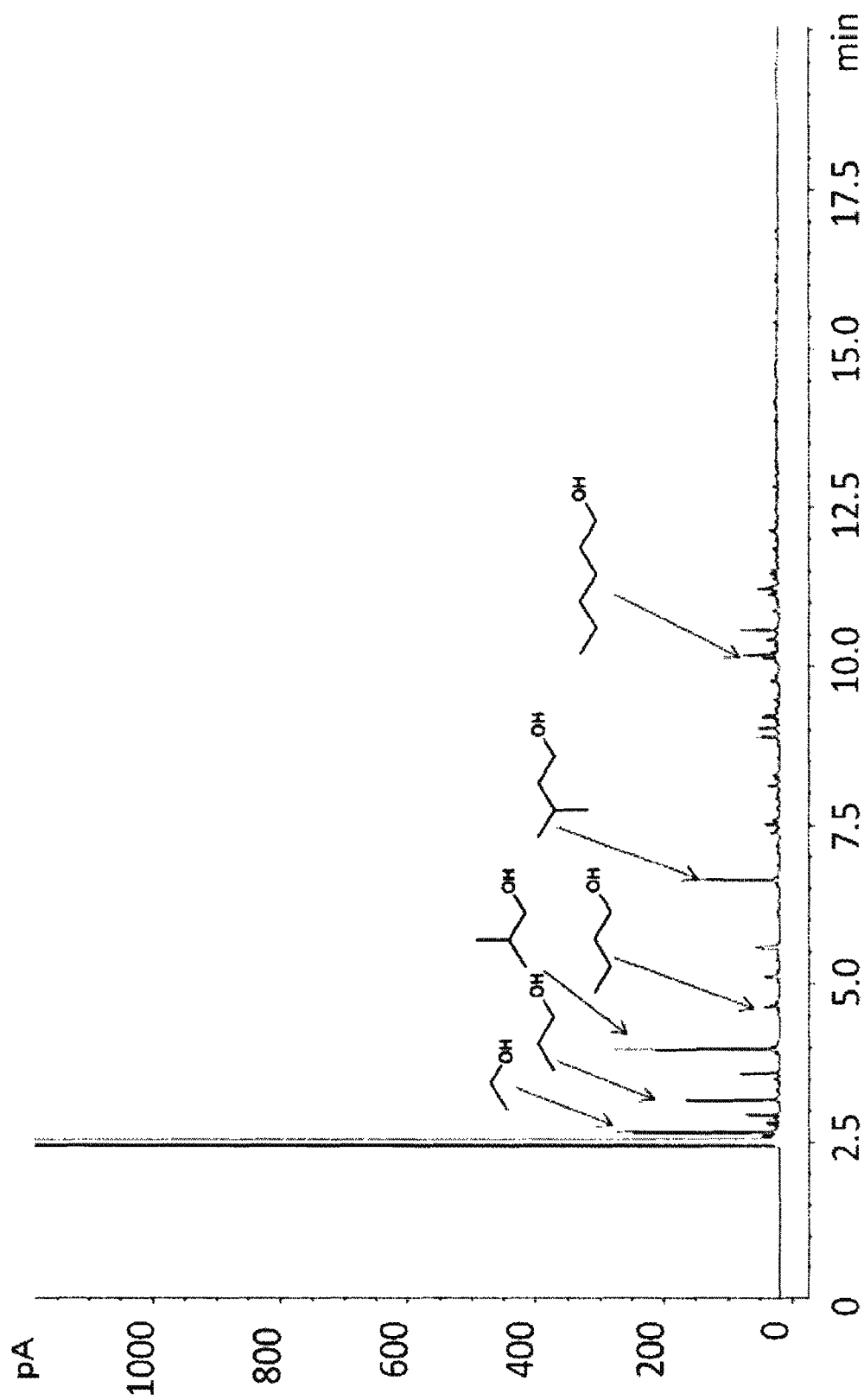
FIG. 3 is a GC-FID trace of distilled liquids from a reaction, with some chemical entities noted.

For comparison, the same experimental procedures as in Example 1 were used, except that the reaction was conducted at 320° C. for 8 hours, Gases were collected by opening the reactor under a water-filled graduated cylinder using the displacement of water to quantify total volume. The distribution of $H_2/CO/CO_2/CH_4$ collected following reaction was 22/6.1/4.7/0.9 mmol. The GC-FID trace of the liquid products of this run is provided in FIG. 3 and indicates that the products comprise a mixture of 5.9/2.0 wt % HAE/CAE in methanol. The extent of conversion was 99%.

According to this example, comparable conversion of solid carbonaceous material may be obtained over a shorter period of operation when the reactions are practiced at a higher temperature.

Example 3

For comparison, the same experimental procedures as in Example 2 were used, except that a commercial sample of 207 mg of ponderosa pine flour (American Wood Fibers, 140 mesh maximum) was substituted for maple. Upon opening the reactor, 30 mmol of a syngas mixture was expelled. Analysis of the liquid products indicated a mixture of 8.4/3.6 wt % HAE/CAE in methanol. The extent of conversion was 96%. In this run, 9 mg of unreacted wood remained after titration.

According to this example, the use of a larger quantity of biomass results in the production of a larger quantity of fluid product. Furthermore, the use of wood derived from coniferous trees is comparable to the use of wood derived from deciduous trees in the reactions.

Example 4

For comparison, the same experimental procedures as in Example 2 were used, except that following the reaction the solid products were washed with methanol and directly recycled into a reaction with 2.4 g $CH_3OH$ and 100 mg of maple sawdust. The extent of conversion for the combined runs was 98%.

According to this example, the solid products of reaction may be advantageously recycled in the reactions.

Example 5

For comparison, the same experimental procedures as in Example 2 were used, except that 100 mg cellulose fibers (Aldrich #C6288) were used instead of wood. Furthermore, 100 mg of a ternary metal oxide catalyst Cu/Zn/Al with 27/53/20 molar ratio ($Cu/ZnO/Al_2O_3$), prepared according to literature procedures and known to be active for enforcing the $CH_3OH \rightleftharpoons CO+2H_2$ and $CO+H_2O \rightleftharpoons CO_2+H_2$ equilibria (5), was used instead of Cu20-PMO. Following reaction, 34 mmol of a syngas mixture was obtained. No intractable material was present following titration of the solids with nitric acid, indicating that the extent of conversion was 100%. The resulting liquid products were found to comprise a solution of roughly 15 wt % HAE in methanol.

According to this example, cellulosic derivatives of woody biomass such as paper may be used in the reactions. It further demonstrates that other methanol synthesis and water gas shift catalysts may be employed in the reactions.

Example 6

For comparison, the same experimental procedures as in Example 2 were used, except that 100 mg of powdered torrefied wood, (wood that had been roasted in an inert atmosphere at 265° C., Energy Institute of the Netherlands, ECN) was used as provided. A 21/4.5/4.8/0.8 mmol mixture of $H_2/CO/CO_2/CH_4$ was collected. The colorless liquid product obtained was a mixture of HAE and CAE (5.8 and 1.4 wt %, respectively) in methanol. The extent of conversion was 89%.

According to this example, solid carbonaceous derivatives of woody biomass may be used in the reactions.

Example 7

A Parr series 5500 compact microreactor equipped with 100 cm³ base was charged with 1.0 g of the same ponderosa pine flour used in example 3, 0.5 g Cu20-PMO, 7.8 g $CH_3OH$, 133 mmol CO, and 40 mmol $H_2$ to generate a net initial pressure of 740 psig. The mixture was heated at 320° C. with stirring (600-800 rpm) for 2.0 hours, 300° C. for 4.0 hours, and then quenched in an ice bath. A maximum autogenous pressure of 2800 psig was generated during reaction. A gaseous mixture containing 139/116/33/2.3 mmol of $H_2/CO/CO_2/CH_4$ was collected following reaction. Analysis of the liquid products by GC-HD indicates a mixture of 10/5.8 wt % HAE/CAE in methanol. The extent of conversion was determined by the method of example 1 to be 85%.

According to this example, the methanol required for conversion may be reduced or supplanted with mixtures of CO and $H_2$ in the reactions.

Example 8

Figure 4:
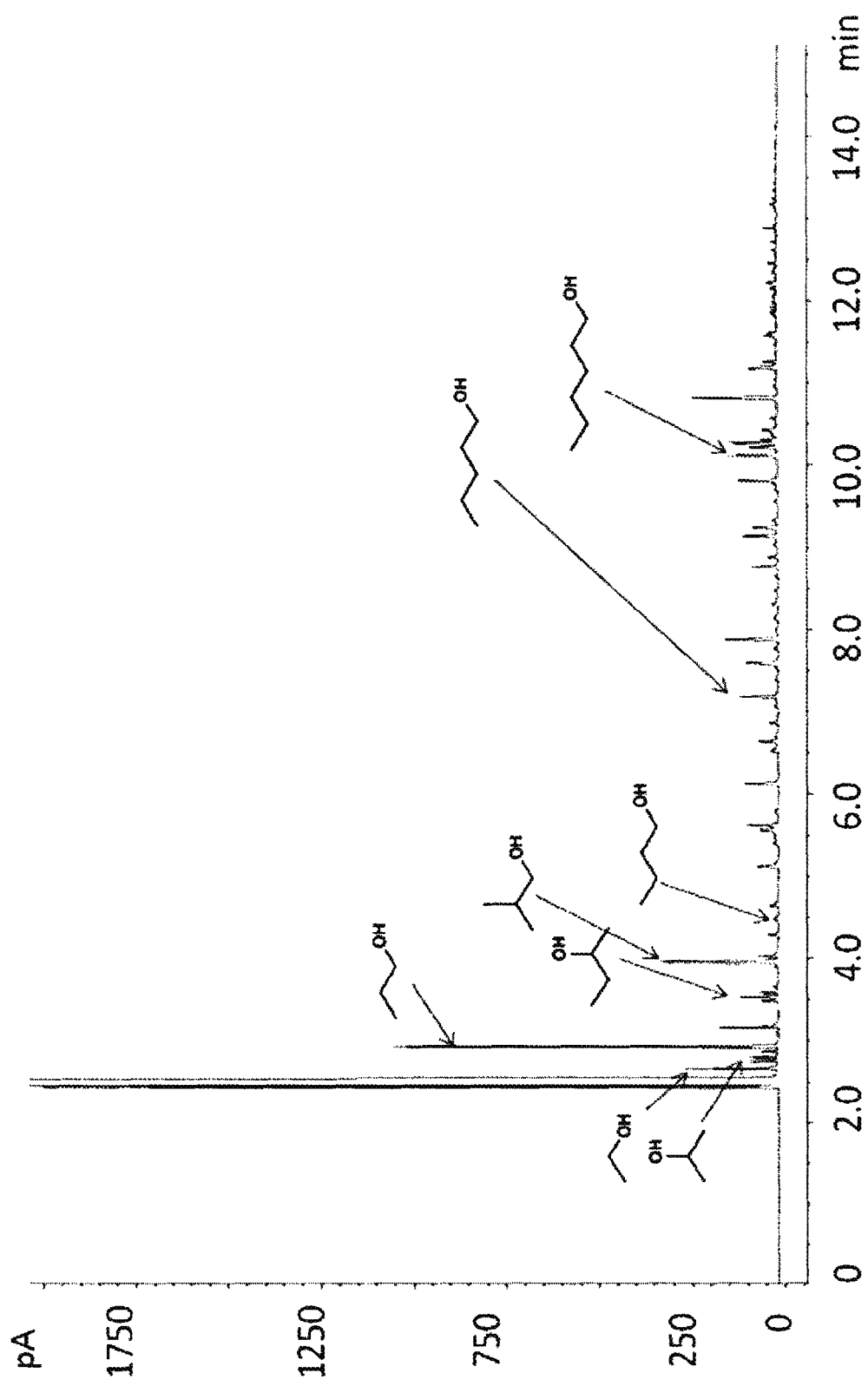
FIG. 4 is GC-FID trace of distilled liquids from a reaction, with some chemical entities noted.

A Parr series 5500 compact microreactor equipped with 100 cm³ base was charged with 6.6 g eucalyptus wood chips obtained having a size between 10-14 mesh, 1.0 g Cu20-PMO, and 15.8 g $CH_3OH$. The mixture was heated at 300° C. with stirring (1000±10 rpm) for 4.5 hours, obtaining an autogenous pressure of 2600 psig, and quenched in an ice bath. Approximately 3.6 g of syngas ($H_2/CO/CO_2/CH_4$=134/4.6/67/15.1 mmol) and 0.5 g volatile organics were collected by room temperature atmospheric distillation into a gas collection bag, 15.6 g of liquids collected by room temperature vacuum distillation at P=0.1 mmHg, 0.8 g methanol-soluble residuals collected by washing residual solids, and 2.5 g solids obtained after washing and drying of the residual solids. The pale yellow distilled liquids were directly subjected to GC-PID analysis, the trace of which is provided in FIG. 4. The liquid distillate consists of 84 wt % of the original methanol and 2.8 g of HAE by integration.

According to this run, large-sized particles of woody biomass may be used in the reactions; a high ratio of wood to methanol may be used in the reactions; and light products of reaction may be separated from heavy products by distillation.

Example 9

A Parr series 5500 microreactor equipped with a 25 cm$^3$ base was charged with 0.75 g cellulose powder (Aldrich #435236), 0.38 g Cu20-PMO, 2.6 g n-$C_5H_{12}$, 54 mmol CO and 58 mmol $H_2$ to obtain a room temperature pressure of 1130 psig. The mixture was heated to 280° C. for a period of 3 hours while stirring at 1000 rpm to a maximum autogenous pressure of 2150 psig, quenched in an ice bath, and the gas phase separated to yield a mixture of 40/35/10/0.1 mmol of a $H_2$/CO/$CO_2$/$CH_4$ syngas mixture. No evidence for chemical reactions of pentane was detected. The extent of conversion of cellulose, as determined by the method of example 1, was 70%.

According to this run, by using a fluidizing cosolvent and mixtures of carbon monoxide and hydrogen in the reactions, an external source of methanol can be reduced or eliminated.

Conclusions

These results, as well as previous studies of cellulose pyrolysis by Shafizadeh and coworkers (6), inform the reaction network proposed in Scheme 1.

Scheme 1

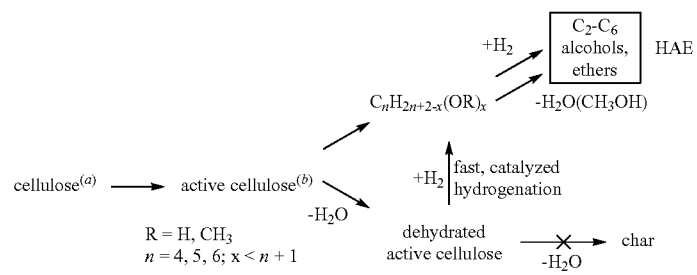

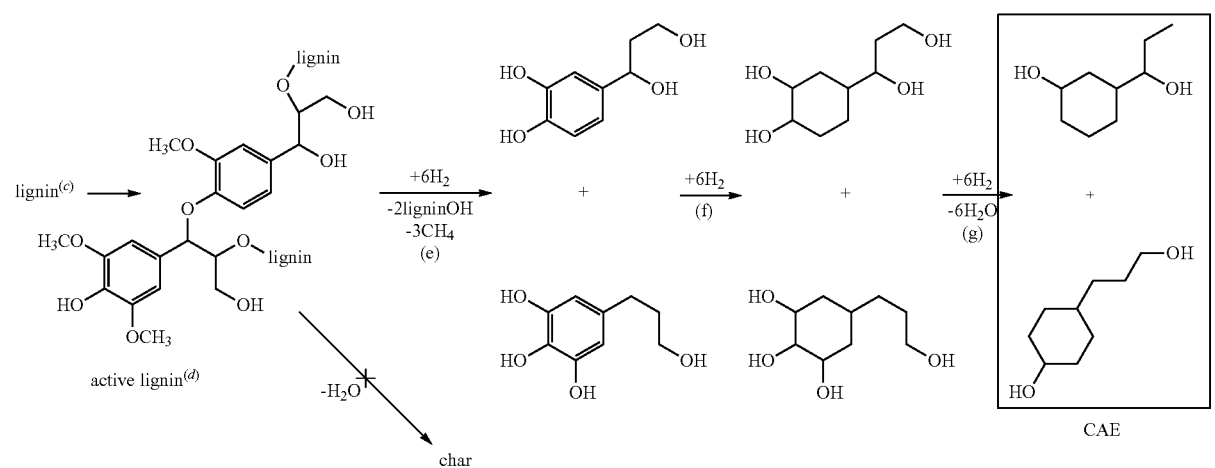

Although not wishing to be bound by the following mechanism, Scheme 1 is a proposed mechanism by which addition of a catalyst prevents char formation: catalyzed conversion of materials to saturated chemical species is much faster than over-dehydration to char; (a) "cellulose" refers to cellulose, hemicellulose, and the cellulosic component of lignocellulose; (b) "active cellulose" consists of soluble oligomers as well as methylated monomers (after Kaliaguine (7)); (c) "lignin" refers to the polymer lignin and to the lignified component lignocellulose (d) active lignin refers to lignified material or to portions of lignified polymers that are soluble (e) depolymerization and demethoxylation by hydrogenolysis (f) aromatic hydrogenation (g) dehydration/hydrogenation.

Example 10

Prophetic

PROCESS MODIFICATION—FOR INCREASING THE RATE OF CONVERSION: By operating at 320° C., significant enhancement in the rate of phase transfer and the rate of conversion to desired products would be obtained.

PROCESS MODIFICATION—FOR DECREASING THE DEMAND FOR METHANOL: One process improvement applicable to any embodiment would be to operate with the minimum or close to the minimum required methanol for stoichiometric conversion. This would decrease the need for methanol and/or methanol recycling.

PROCESS MODIFICATION—FOR DECREASING THE DEMAND FOR METHANOL: We anticipate that this process could be operated continuously with an input of biomass+methanol and an output of fluid product+syn gas. One process improvement applicable to any embodiment would be to operate continuously with an input of biomass+hydrogen+carbon monoxide and an output of fluid product+syn gas. This would decrease the need for methanol and/or methanol recycling.

PROCESS MODIFICATION—FOR SELECTIVE PRODUCTION OF AROMATICS: For commodity chemicals such as BTX or for jet fuels, aromatics are extremely desirable. It is known from the literature that under hydrothermal (non-methanolic) conditions and high pressures of hydrogen, $Rh/ZrO_2$ will catalyze the hydrogenolysis of hydroxyl groups on aromatic rings under hydrothermal conditions to produce water and deoxygenated aromatics (8). This catalyst can be used in addition to a Cu-doped metal oxide. The rate of hydrogenation of non-oxygenated aromatics is dramatically slower relative to the rate of hydrogenation of oxygenated aromatics, so isolating fully-deoxygenated aromatics is anticipated.

PROCESS MODIFICATION—FOR RECOVERY OF METHANOL: Selective chain degradation of cellulose to hydrogen and carbon monoxide, under conditions wherein the equilibria $CH_3OH=CO+2H_2$ and $CO+H_2O=CO_2+H_2$ is enforced, would allow for the recovery of methanol via the following:

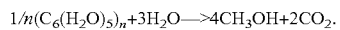

$$1/n(C_6(H_2O)_5)_n + 3H_2O \rightarrow 4CH_3OH + 2CO_2.$$

This could be accomplished using $Pt/Al_2O_3$ or $W_2C$ on activated carbon in addition to a Cu-doped metal oxide.

Recovery of the methanol in practicing any embodiment would allow for this process to be deployed near the site of biomass growth, dramatically reducing the costs of biomass transport.

REFERENCES

The following publications are hereby incorporated by reference herein:

1. Perlack, R. D.; Wright, L. L.; Turhollow, A. F.; Graham, R. L.; Stokes, B. J.; Erbach, D. C. *Biomass as Feedstock for a Bioenergy and Bioproducts Industry: The Technical Feasibility of a Billion-Ton Annual Supply*, Report No. DOE/GO-102995-2135; Oak Ridge National Laboratory: Oak Ridge, Tenn., 2005; on the world wide web at osti.gov/bridge.
2. Huber, G. W.; Iborra, S.; Corma, A. *Chemical Reviews* 2006, 106, 4044-4098.
3. Milne, T. A.; Evans, Abatzoglou, N. *Biomass Gasifier Tars: Their Nature, Formation and Conversion*; Report No. NREL/TP-570-25357; National Renewable Energy Laboratory: Golden, Colo., 1998; on the world wide web at osti.gov/bridge.
4. Macala, G. S.; Matson, T. D.; Johnson, C. L.; Lewis, R. L.; Iretskii, A. V.; Ford, P. C. *ChemSusChem* 2009, 2, 215-217.
5. Herman, R. G.; Klier, K.; Simmons, G. W.; Finn, B. P.; Bulko, J, B.; Kobylinski, T. P. *Journal of Catalysis* 1979, 56, 407-429.
6. Bradbury A. G. W.; Sakai, Y.; Shafizadeh, F. *J. Appl. Polym. Sci.* 1979, 23, 3271-3280.
7. Poirier, M. G; Ahmed, A.; Grandmaison, J-L.; Kaliaguine, S. C. F. *Ind. Eng. Cheers. Res.* 1987, 26, 1738-1743.
8. Gutierrez, A.; Kaila, R. K.; Honkela, M, L.; Slioor, R. Krause, A. O. I. *Catalysis Today* 2009, 147, 239-246.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims.

What is claimed is:

1. A method of catalytically preparing a fluid product from biomass containing lignin, cellulose, hemicellulose or lignocellulose, or any combination thereof, comprising:
   reacting a biomass material in a reducing environment in the presence of at least one of a cosolvent or methanol and one or more catalysts so as to produce a fuel or fuel additive fluid product, wherein the one or more catalysts establish both of the following equilibria:

Cosolvent or methanol=$CO+2H_2$,      a)

$CO+H_2O=CO_2+H_2$.      b)

2. The method of claim 1, wherein the fluid product is comprising a high-octane gasoline additive containing at least one of methanol or $C_5$-$C_9$ aliphatic alcohols.

3. The method of claim 1, wherein the one or more catalysts is selected from a group consisting of a Cu-doped metal oxide, a zeolite-based catalyst, a supported metal catalyst, a metal carbide catalyst, a zeolite catalyst, and any combination thereof.

4. The method of claim 3, wherein the Cu-doped metal oxide is selected from the group consisting of oxides of Cu, M(II), M(III) and a combination thereof, in any proportion, wherein M(II) is selected from Mg and/or Zn, and M(III) is selected from Al, Cr, and/or Fe; the zeolite or zeolite-based catalyst is H-ZSM-5; the supported metal catalyst is selected from the group consisting of $Pt/Al_2O_3$, $Rh/ZrO_2$, Pd/C, and Cu/hydrotalcite; and the metal carbide catalyst is $W_2C$ supported on activated carbon; and any combination thereof.

5. The method of claim 1, further comprising:
depolymerizing polymeric material in the presence of one or more depolymerization catalysts, the polymeric material contained in or derived from the biomass; or
dehydrating chemical compounds in the presence of one or more dehydration catalysts, the chemical compounds derived from the biomass; or
hydrogenating chemical intermediates in the presence of one or more hydrogenation catalysts, the chemical intermediates derived from the biomass; or a combination thereof.

6. The method of claim 5, wherein the one or more catalysts is selected from the group consisting of a Cu-doped metal oxide, a zeolite-based catalyst, a supported metal catalyst, a metal carbide catalyst, a zeolite catalyst, and a combination thereof; the one or more depolymerization catalysts is selected from the group consisting of a copper-doped metal oxide catalyst, a supported metal catalyst, and a combination thereof; the one or more dehydration catalysts is selected from the group consisting of a Cu-doped metal oxide, a zeolite catalyst, and a combination thereof; and the one or more hydrogenation catalysts is selected from the group consisting of a Cu-doped metal oxide, a supported metal catalyst, a metal carbide catalyst, and a combination thereof.

7. The method of claim 6, wherein the Cu-doped metal oxide or Cu-doped metal oxide catalyst is selected from the group consisting of oxides of Cu, M(II), M(III), and a combination thereof, in any proportion, wherein M(II) is selected from Mg and/or Zn, and M(III) is selected from Al, Cr, and/or Fe; the zeolite catalyst is H-ZSM-5; the supported metal catalyst is selected from the group consisting of Pt/Al$_2$O$_3$, Rh/ZrO$_2$, Pd/C, and Cu/hydrotalcite; and the metal carbide catalyst is W$_2$C supported on activated carbon; and any combination thereof.

8. The method of claim 5, wherein the one or more catalysts, the one or more depolymerization catalysts, the one or more dehydration catalysts, and the one or more hydrogenation catalysts are the same catalyst.

9. The method of claim 8, wherein the same catalyst comprises mixed oxides of Cu/Mg/Al or Cu/ZnO/Al$_2$O$_3$.

10. The method of claim 1, wherein CO and H$_2$ replace the methanol or are added in addition to the methanol.

11. The method of claim 1, wherein the fluid product comprises a C$_5$, C$_6$, C$_7$, C$_8$ or C$_9$ alcohol, or a combination thereof.

12. A method of catalytically preparing a fluid product from solid carbonaceous material wherein the solid carbonaceous material comprises coal, mineral fuels, plastics, or any combination thereof, comprising:
reacting solid carbonaceous material in the presence of one or more first catalysts to produce soluble material under conditions in which both of the following equilibria are established by the one or more first catalysts:

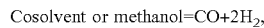  a)

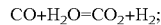  b)

depolymerizing polymeric material in the presence of one or more depolymerization catalysts, the polymeric material contained in or derived from the solid carbonaceous material;
dehydrating chemical compounds in the presence of one or more dehydration catalysts, the chemical compounds derived from the solid carbonaceous material; and
hydrogenating chemical intermediates in the presence of one or more hydrogenation catalysts, the chemical intermediates derived from the solid carbonaceous material;
whereby to produce a fluid product.

13. The method of claim 12, further comprised of at least one of CO and H$_2$, cosolvent or methanol.

14. The method of claim 12, wherein the one or more first catalysts is selected from the group consisting of a Cu-doped metal oxide, a zeolite-based catalyst, a supported metal catalyst, a metal carbide catalyst, a zeolite catalyst, and a combination thereof; or the one or more depolymerization catalysts is selected from the group consisting of a copper-doped metal oxide catalyst, a supported metal catalyst, and a combination thereof; or the one or more dehydration catalysts is selected from the group consisting of a Cu-doped metal oxide, a zeolite catalyst, and a combination thereof or the one or more hydrogenation catalysts is selected from the group consisting of a Cu-doped metal oxide, a supported metal catalyst, a metal carbide catalyst, and a combination thereof or any combination thereof.

15. The method of claim 14, wherein the Cu-doped metal oxide or Cu-doped metal oxide catalyst is selected from the group consisting of oxides of Cu, M(II), M(III), and a combination thereof, in any proportion, wherein M(II) is selected from Mg and/or Zn, and M(III) is selected from Al, Cr, and/or Fe; the zeolite catalyst is H-ZSM-5; the supported metal catalyst is selected from the group consisting of Pt/Al$_2$O$_3$, Rh/ZrO$_2$, Pd/C, and Cu/hydrotalcite; and the metal carbide catalyst is W$_2$C supported on activated carbon; and any combination thereof.

16. The method of claim 12, wherein the one or more first catalysts, the one or more depolymerization catalysts, the one or more dehydration catalysts, and the one or more hydrogenation catalysts are the same catalyst.

17. A method of catalytically preparing a fluid product from biomass containing lignin, cellulose, hemicellulose or lignocellulose, or any combination thereof, comprising:
reacting a biomass material in a reducing environment in the presence of at least one of a cosolvent and mixtures of carbon monoxide and hydrogen and one or more catalysts so as to produce a fuel or fuel additive fluid product, wherein the one or more catalysts establish an equilibria of CO+H$_2$O=CO$_2$+H$_2$.

18. The method of claim 17, wherein the fluid product is comprising a high-octane gasoline additive containing at least one of methanol or C$_5$-C$_9$ aliphatic alcohols.

19. The method of claim 17, wherein the one or more catalysts is selected from the group consisting of a Cu-doped metal oxide, a zeolite-based catalyst, a supported metal catalyst, a metal carbide catalyst, a zeolite catalyst, and any combination thereof.

20. The method of claim 19, wherein the Cu-doped metal oxide is selected from the group consisting of oxides of Cu, M(II), M(III), and a combination thereof, in any proportion, wherein M(II) is selected from Mg and/or Zn, and M(III) is selected from Al, Cr, and/or Fe; the zeolite or zeolite-based catalyst is H-ZSM-5; the supported metal catalyst is selected from the group consisting of Pt/AhO$_3$, Rh/ZrO$_2$, Pd/C, and Cu/hydrotalcite; and the metal carbide catalyst is W$_2$C supported on activated carbon; and any combination thereof.

21. The method of claim 17, further comprising:
depolymerizing polymeric material in the presence of one or more depolymerization catalysts, the polymeric material contained in or derived from the biomass; or dehydrating chemical compounds in the presence of one or more dehydration catalysts, the chemical compounds derived from the biomass; or hydrogenating chemical intermediates in the presence of one or more hydrogenation catalysts, the chemical intermediates derived from the biomass; or a combination thereof.

22. The method of claim 21, wherein the one or more catalysts is selected from the group consisting of a Cu-doped metal oxide, a zeolite-based catalyst, a supported metal catalyst, a metal carbide catalyst, a zeolite catalyst, and a combination thereof; the one or more depolymerization catalysts is selected from the group consisting of a copper-doped metal oxide catalyst, a supported metal catalyst, and a combination thereof; the one or more dehydration catalysts is selected from the group consisting of a Cu-doped metal oxide, a zeolite catalyst, and a combination thereof; and the one or more hydrogenation catalysts is selected from the group consisting of a Cu-doped metal oxide, a supported metal catalyst, a metal carbide catalyst, and a combination thereof.

23. The method of claim 22, wherein the Cu-doped metal oxide or Cu-doped metal oxide catalyst is selected from the group consisting of oxides of Cu, M(II), M(III), and a combination thereof, in any proportion, wherein M(II) is selected from Mg and/or Zn, and M(III) is selected from Al, Cr, and/or Fe; the zeolite catalyst is HZSM-5; the supported metal catalyst is selected from the group consisting of $Pt/Al_2O_3$, $Rh/ZrO_2$, Pd/C, and Cu/hydrotalcite; and the metal carbide catalyst is $W_2C$ supported on activated carbon.

24. The method of claim 22, wherein the one or more catalysts, the one or more depolymerization catalysts, the one or more dehydration catalysts, and the one or more hydrogenation catalysts are the same catalyst.

* * * * *